United States Patent [19]

Yoshino et al.

[11] Patent Number: 4,597,650
[45] Date of Patent: Jul. 1, 1986

[54] SPECULAR MICROSCOPE

[75] Inventors: Hisakazu Yoshino; Kazutoshi Takagi, both of Tokyo, Japan

[73] Assignee: Tokyo Kogaku Kikai Kabushiki Kaisha, Tokyo, Japan

[21] Appl. No.: 494,190

[22] Filed: May 13, 1983

[30] Foreign Application Priority Data

May 19, 1982 [JP] Japan ................... 57-84387

[51] Int. Cl.⁴ ............................................. A61B 3/10
[52] U.S. Cl. ............................ 351/214; 351/208
[58] Field of Search ............... 351/208, 209, 210, 211, 351/214, 212; 354/62

[56] References Cited

U.S. PATENT DOCUMENTS 4,253,743 3/1981 Matsumura ................... 351/208
4,396,260 8/1983 Iakizawa et al. .

FOREIGN PATENT DOCUMENTS 3150124 12/1981 Fed. Rep. of Germany .
1951159 10/1969 Japan .
22-63650 12/1972 Japan .
55-110532 8/1980 Japan .

Primary Examiner—John K. Corbin
Assistant Examiner—P. M. Dzierzynski
Attorney, Agent, or Firm—Brumbaugh, Graves, Donohue & Raymond

[57] ABSTRACT

A specular microscope in which the image of a slit aperture of an illumination optical system is formed at an endothelial cell layer of an eye to be examined and including a light intercepting plate having a main aperture and additional apertures adjacent said main aperture so that an image of the endothelial cell layer is formed at said main aperture and a reflection light reflected by a corneal surface of the eye is transmitted through said additional apertures of said light intercepting plate.

5 Claims, 4 Drawing Figures

SPECULAR MICROSCOPE

BACKGROUND OF THE INVENTION (1) Field of the Invention

This invention relates to a specular microscope for observing and/or photographing the endothelial cells of the cornea.

(2) Description of the Prior Art

There are hexagonal cells having a size of about 20 μm called endothelial cells behind the cornea of the human eye, these play a vital role in maintaining the transparency of the cornea. As surgical microscopes, etc., have been developed and become wide-spread in recent years, techniques of eye surgery have also made remarkable progress, and surgical operations such as of the vitreous body, ultrasonic surgical operations of cataracts, implantation of corneas, implantation of artificial crystalline lenses, and the like are carried out daily. Since surgical instruments come into contact with the eye being operated on, and perfusion solutions such as physiological salt solutions, Ringer's solution, or the like affect the endothelial cellular membrane of the cornea, the transparency of the cornea is reduced after such a surgical operation and this causes the problem of a drop in the visual acuity. For this reason, it has become important to observe and/or photograph the endothelial cells of the cornea in vivo so as to measure and inspect their changes.

To comply with this demand, an instrument called a specular microscope has been developed and put into practical application as an apparatus for observing and photographing the endothelial cells of the cornea. In the specular microscope, illuminating light beams are projected onto the cornea through a slit-illuminating optical system so as to form a slit image on the endothelial cell layer of the cornea. The illuminating light beams are subjected to mirror reflections at the endothelial cell layer of the cornea, and are emitted from the eye to form reflected light beams. The specular microscope is designed to detect these reflected beams to observe and photograph an image of the endothelial cells of the cornea.

The cornea is usually a light-transmitting member and the reflectivity of the endothelial cells is extremely low. For this reason, the specular microscope is designed so that it utilizes the mirror reflection at the endothelial cell layer of the cornea for observing and photographing the endothelial cells, as described above. To this end, the slit-illuminating optical axis and the optical axis of the reflected light beams are symmetrical with each other with respect to a normal line the illuminated member, that is, to the portion being observed.

However, it should be noted that the reflectivity of the surface of the cornea is by far greater than that of the endothelial cells of the cornea. In fact, the reflectivity of the endothelial cell layer is approximately 0.02% whereas the reflectivity of the surface of the cornea is approximately 2.5%. Moreover, the cornea is extremely thin. For these reasons, the light beams reflected at the surface of the cornea enter the visual field of observation of the specular microscope. As a result, the image of the light reflected at the upper surface of the cornea partially overlaps the image of the endothelial cells and the image of the light scattered from the cornea. Thus, there is produced a critical problem that observation of the endothelial cells of the cornea is adversely affected.

It should further be noted that conventional specular microscopes have been designed as a mono-functional single-purpose instrument which can only be used for observation and photography of the endothelial cells of the cornea, regardless of whether it is of a contact type or a non-contact type. In view of the fact, a proposal has been made by Shiro Takizawa and Shinichi Nishimura in U.S. patent application Ser. No. 122,673 dated Feb. 19, 1980 now U.S. Pat. No. 4,396,260 which is assigned to the same assignee as the present application on a slit lamp which can also be used as a specular microscope simply by replacing the objective lens of an observation microscope of the slit lamp by an attachment for a specular microscope. This slit lamp is characterized by the fact that the illumination of the endothelial cells of the cornea is effected through the slit-illuminating system of the slit lamp. The proposed instrument has been found disadvantageous in that it is difficult to position the optical axis of the observation microscope and the optical axis of the slit-illuminating system symmetrical with each other with respect to the normal line of the portion being inspected. Thus, it is very difficult to establish an alignment in which mirror reflection at the endothelial cells is introduced into the observation microscope.

Furthermore, in view of the fact that whether or not the endothelial cells of the cornea have been modified by a surgical operation is determined by calculating the number of endothelial cells per unit area or by measuring the size of individual cells or the distribution of cell sizes, graduated lines are provided within the observation microscope of the specular microscope, or graduated lines are simultaneously photographed together with the endothelial cells. The conventional graduated lines are formed by vacuum evaporation of aluminum onto a glass plate and appears as black lines within the visual field so that it is difficult to distinctly observe them the faint images of the endothelial cells. Since the graduated lines must be photographed so that their images are produced over the images of the endothelial cells when a photograph is to be taken, as that the images of the graduated lines become an obstacle to the resulting photograph.

SUMMARY OF THE INVENTION

The present invention is directed to eliminate the problems with the conventional specular microscope described above.

It is a first object of the present invention to provide a specular microscope which can reduce harmful light reflected from the surface of the cornea and make it possible to observe and/or photograph more sharply the endothelial cells of the cornea.

It is a second object of the present invention to provide a specular microscope which makes it extremely easy to align a desired portion of the endothelial cells of the cornea with the visual field of an observing optical system.

It is a third object of the present invention to provide a specular microscope which makes it easier than in a conventional specular microscope to view reference graduations necessary for obtaining a unit area of the field for counting the number of endothelial cells of the cornea, and prevent the reference graduations from overlapping the image of the endothelial cells of the cornea to makes it possible to observe and/or record the endothelial cells of the cornea.

It is a fourth object of the present invention to provide an attachment which can accomplish at least one of the first and third objects described above and which can be attached to a conventional general slit lamp so that it can be used as a specular microscope.

According to the present invention, the above and other objects can be accomplished by providing an objective lens which at first forms an image of the light reflected at the endothelial cells of the cornea at an intermediate image-forming point, and an aperture plate having a main aperture adapted to be located at the image-forming point and alignment apertures adjacent to the outer periphery of the main aperture, and main and alignment apertures being located with each other so that when the light reflected at the surface of the cornea passes through the alignment aperture, the light reflected at the endothelial cells of the cornea can pass through the main aperture. According to this arrangement, when the light reflected at the surface of the cornea reaches the alignment aperture, the light reflected at the endothelial cells of the cornea automatically passes through the main aperture so that not only does the alignment become extremely easy, but most of the harmful light reflected at the corneal surface is intercepted by the aperture plate because the slit opening is thin, and hence it does not prevent observation of and photographing the endothelial cells of the cornea.

The alignment aperture may consist of a plurality of slits formed along the periphery of the main aperture at predetermined spacings, they can be used as a scale as they permit the passage of the light reflected from the surface of the cornea, and the graduated lines may thus be formed and such lines does not overlap the image of the endothelial cells of the cornea formed through the main aperture.

DESCRIPTION OF THE PREFERRED EMBODIMENTS

Hereinafter, preferred embodiments of the present invention will be described with reference to a non-contact type of specular microscope, by way of example, but the present invention can also be applied as such to a contact type specular microscope.

Figure 1:
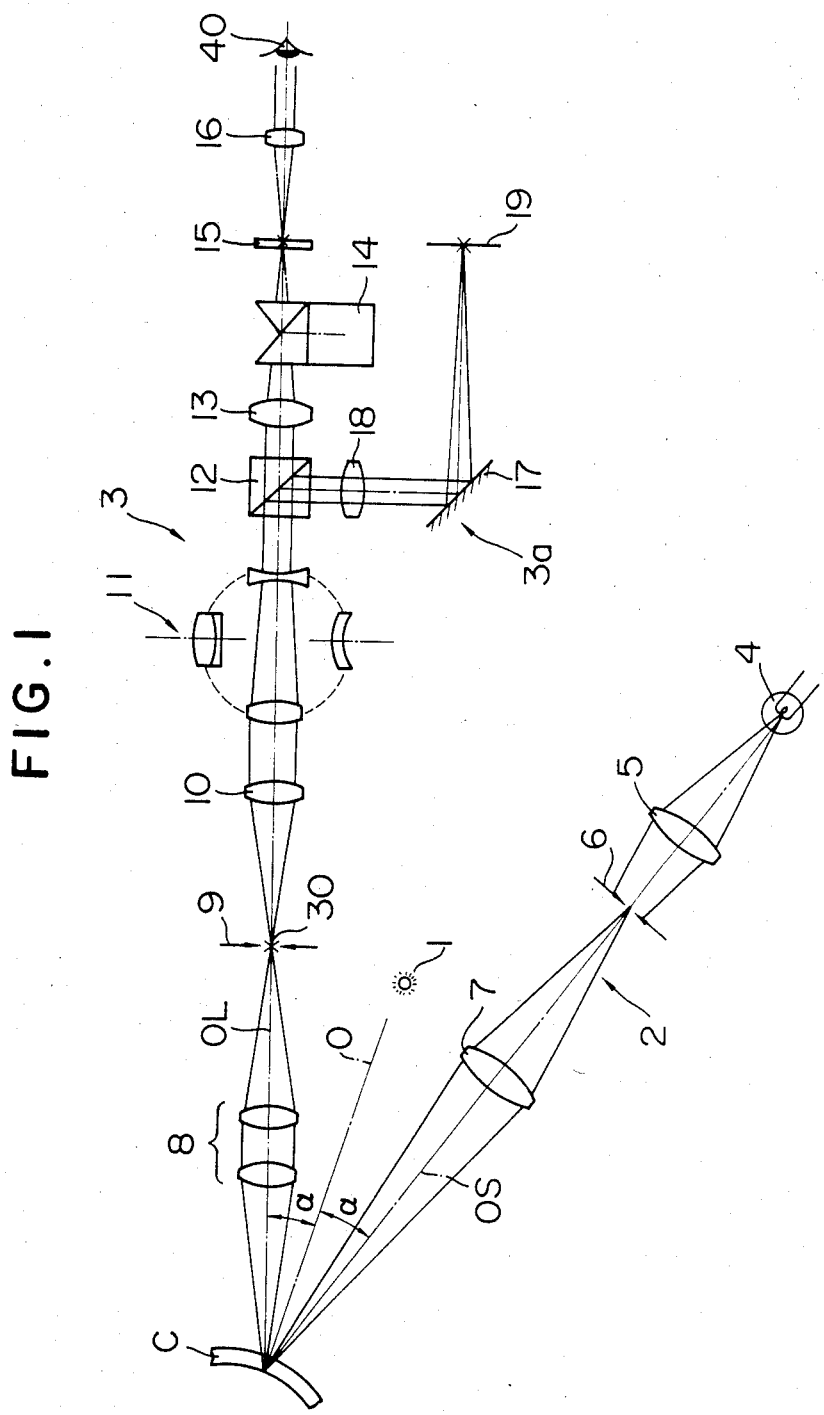
FIG. 1 is a diagrammatical illustration of an optical system in accordance with a first embodiment of the present invention.

Referring to the drawings, particularly to FIG. 1, there is shown an optical system of a specular microscope including a fixed visual target 1, an illuminating optical system 2 and an observation/photographing optical system 3. The fixed visual target 1 is a small lamp which may be carried by a multi-jointed or flexible arm, not shown, and can move freely in three-dimensional directions. The optical axis O of the patient's eye can be fixed by making the eye see fixedly this fixed visual target 1. The illuminating optical system 2 consists of a lamp 4, a condenser lens 5, a slit aperture 6 and a projection lens 7 that are disposed coaxially. The image of the slit aperture 6 is formed and projected onto the endothelial cell layer of the cornea C of the patient's eye by the projection lens 7.

The observation/photographing optical system 3 consists of an objective lens 8, and aperture plate 9, a relay lens 10, a variable power lens system 11, a beam splitter 12, an image-forming lens 13, an inverting prism 14, a focus plate 15 and an ocular lens 16, that are disposed coaxially. The light beams separated by the beam splitter 12 reaches a film 19 through a photographing optical system 3a consisting of a mirror 17 and an imaging lens 18. The focus plate 15 of the observation optical system and the film 19 of the photographing optical system are conjugate to each other. The optical axis OS of the illuminating optical system 2 and the optical axis OL of the observation optical system are disposed to make the same angle with respect to the optical axis O of the eye. Both optical systems are integrally held by mechanical support means (not shown) so that they can be focused onto the endothelial cells of the cornea by moving the support means back and forth.

Figure 2:
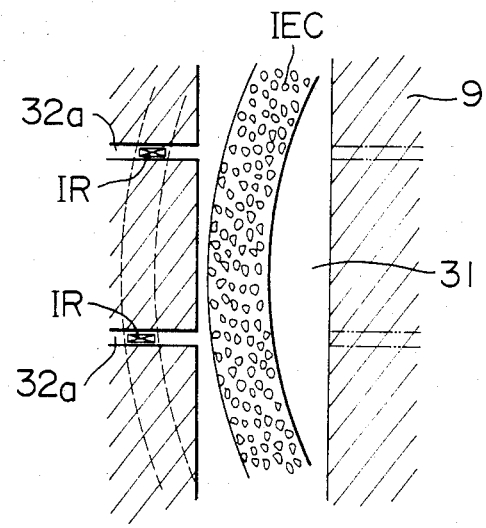
FIG. 2 is a plan view showing one example of an aperture plate in the first embodiment of the present invention.

As shown in FIG. 2, the aperture plate 9 consists of a main aperture 31 which is of an elongated configuration extending in the longitudinal direction and thin slit apertures 32a which are perpendicular to the longitudinal direction of the main aperture 31. The slit apertures 32a constitute alignment apertures. The aperture plate 9 is disposed at an intermediate image-forming point 30 of the endothelial cells of the cornea by the objective lens 8 of the photographing optical system 3.

In operation the line of sight of the patient's eye is at first fixed by making the eye to gaze fixedly at the fixed visual target 1. The illumination lamp 4 of the illuminating optical system is then turned on so as to illuminate the eye by a slit light beam. The instrument is then adjusted in position so that the strong light IR reflected at the surface of the cornea is incident on the plate 9. The instrument is then finely adjusted so that the strong light IR reflected at the surface of the cornea leaks slightly through the slit apertures 32a. In this manner, only the reflections at the endothelial cells of the cornea can pass through the main aperture 31. In this position, substantial part of the light reflected at the surface of the cornea is intercepted by the plate 9. Under this condition, the instrument is moved finely back and forth so that the image of the endothelial cells of the cornea can be focused and observed, and can be recorded on the film 19, if necessary.

As described above, this embodiment makes positive use of the strong reflected light from the upper surface of the cornea that has been conventionally believed to be harmful light. An image is formed by the light reflected at the endothelial cells of the cornea in the main aperture 31 when the light reflected at the surface of the cornea is incident on the slit apertures, so that alignment can be done extremely easily. Moreover, since the slit apertures can be formed to be extremely thin, most of the harmful light reflected at the surface of the cornea can be intercepted. Accordingly, this embodiment provides the advantage that observation and photographing of the endothelial cells of the cornea can be done more clearly than that by a conventional specular microscope. Although the alignment apertures are illustrated as being in the form of slits in this embodiment, the shapes of the alignment apertures are not limited to the illustrated configurations but may be round, square or any other shapes.

Figure 3:
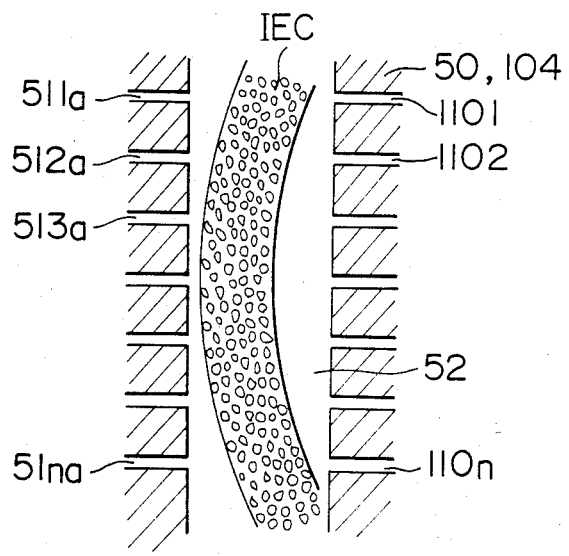
FIG. 3 is a plan view showing another example of the aperture plate.

Referring to FIG. 3, it will be noted that the embodiment shown therein includes an aperture plate 50 which is intended to be used in the place of the plate 9 in the previous embodiment. The plate 50 has an elongated main aperture 52 and a plurality of thin slit apertures 511a, 512a, 513a, . . . , 51na which are formed equidistantly in the plate 50 with predetermined spacings. Since these slit apertures are illuminated by the light reflected at the surface of the cornea, the operator can observe them as if they were graduation lines, and since they can be photographed onto the film, they are extremely convenient for calculations concerning the endothelial cells of the cornea.

Since the slit apertures are formed sideways from the main aperture 52 of the plate 50 in which the image of the endothelial cells of the cornea is to be formed, the graduated lines formed by the slit apertures never overlap the image of the endothelial cells of the cornea. Accordingly, they are easy to use for observation and calculation but do not erase even a part of the invention on the endothelial cells of the cornea.

Referring back to FIG. 1, it will be noted that the plate 9 is disposed in front of the variable power lens 11. The plate 9 is also the intermediate image-forming point 30 and conjugate with the focus plate 15 and the film 19. Therefore, when the magnification of the observed image or the photographic image is changed by the variable power lens system 11, the spacings between the slit openings 511a, 512a, 513a, . . . , 51na used as graduations change with the same magnification, and the slit apertures are observed and photographed at the same magnification. If a change with time of the number of endothelial cells within a unit area is to be examined, this arrangement provides the following advantage. Namely, even if photographing is effected one time at a different magnification from that of the previous photographing, the graduation spacing on the respective photographs correspond to the same spacing on the endothelial cell layer of the eye being examined, and the reference unit area can be determined on the basis of the graduation spacing photographed, without causing any substantial change of the unit area.

The present invention should not be limited to its application to a specular microscope as illustrated in the above embodiments. As previously proposed in the above U.S. patent application Ser. No. 122,673, the present invention can be constructed as an attachment apparatus to be fitted onto a general photo slit lamp.

Figure 4:
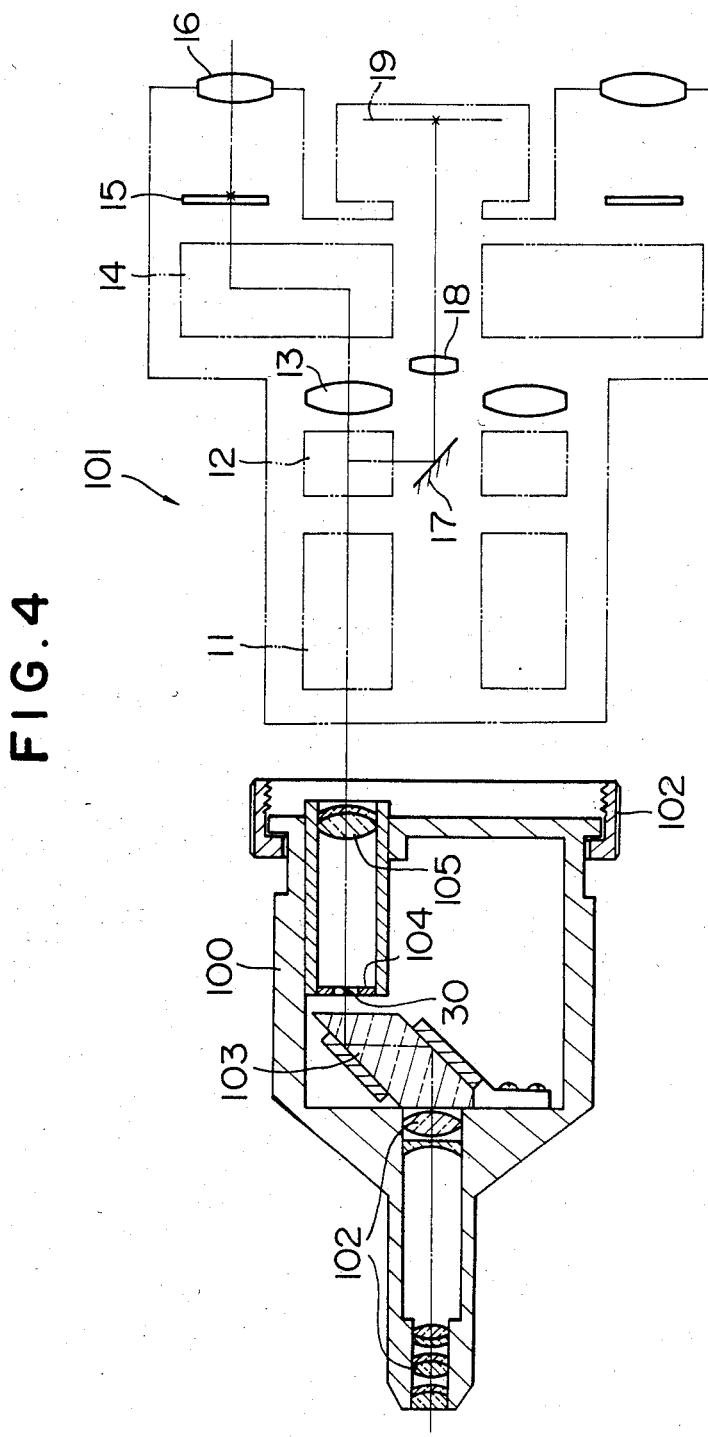
FIG. 4 is a horizontal sectional view of a third embodiment of the present invention.

Referring to FIG. 4, there is shown a further embodiment having at attachment provided with a casing 100 which has ring nut 102 adapted to be fitted to an observation microscope 101 of a slit lamp. In order that this attachment be attached to the slit lamp, the objective lens of the slit lamp be at first removed and the attachment casing 100 is fitted to the slit lamp by the ring nut 102.

The attachment casing 100 contains an optical system consisting of an objective lens system 102, a reflecting prism 103, an aperture plate 104 and a relay lens 105, and is used for observing and photographing the endothelial cells of the cornea by leading light from the endothelial cells onto one of the optical systems of the observation microscope 101 of the slit lamp. In this type of instrument, the concept of the present invention can be applied to the plate 104.

When this attachment is fitted to a slit lamp and is used as a specular microscope, the slit illumination means of the slit lamp may be used for illuminating the endothelial cells of the cornea. In FIG. 4, the observing and photographing optical system is shown with the same reference numerals as in FIG. 1. In this case, since a slit illumination system can be moved either to the right or to the left with respect to the observation microscope, it will be convenient to provide slit apertures 1101, 1102, . . . , 110n at the side opposite to the side where the slit apertures 32a or 51na are formed as shown by phantom lines in FIGS. 2 and 3. Then, the apparatus can be used on whichever side the slit illumination system is positioned.

The invention has thus been shown and described with reference to specific embodiments, however, it should be noted that the invention is in no way limited to the details of the illustrated arrangements but changes and modifications may be made without departing from the scope of the appended claims.

What is claimed is:

1. A specular microscope comprising an illumination optical system and an observation optical system, said illumination optical system including a light source, a substantially straight line slit aperture for passing a part of light beams radiated from said light source and a projecting lens for forming an image of said slit aperture, said light source, said slit aperture and said projecting lens being arranged in this order along an optical axis;

said observation optical system including an objective lens system for forming an image at an intermediate image-forming point, an image-forming optical system for forming an observing image from the image in said intermediate image-forming point, and an ocular optical system for observing the images;

said observation optical system having an optical axis intersecting at an angle the optical axis of said illumination optical system at the image of said alit aperture; and light intercepting means provided at said intermediate image-forming point and including substantially straight line main aperture means disposed on the optical axis of said observation optical system, and alignment aperture means disposed adjacent said main aperture means comprising substantially straight line apertures extending transverse to the substantially straight line main aperture and offset from the optical axis of said observation optical system; the main aperture being positioned to intercept the light reflected from the cornea and to pass light reflected from the endothelial cells, and the alignment aperture means being positioned to partially transmit light reflected from the cornea;

whereby when the specular microscope is positioned so that an image of said slit aperture of said illumination optical system is formed at an endothelial cell layer of an eye to be examined, an image of the endothelial cell layer is formed at said main aperture means of said light intercepting means and light reflected by a corneal surface of the eye to be examined is partially transmitted through said alignment aperture means and is substantially intercepted by the said light intercepting means.

2. A specular microscope as set forth in claim 1 wherein said intercepting means includes a plate having the main aperture means and wherein said substantially straight line apertures in the alignment aperture means include at least two slit-like openings perpendicular to said main aperture means with a spacing between said slit-like openings being of a predetermined value so that they can be used as a scale.

3. A specular microscope as set forth in claim 1 wherein said image-forming optical system includes a light splitting means and a photographing optical system for forming an image of light separated by said splitting means on a recording medium.

4. An attachment means for installation on a slit lamp which has slit-illuminating means having an optical axis for illuminating with a slit of light an eye to be examined, and observation optical means having an optical axis for inspecting the illuminated portion of the eye being examined;

said attachment comprising an optical axis which can coincide with said optical axis of the observation optical means when said attachment is installed on the slit lamp, an objective lens system for forming an image at an intermediate image-forming plane thereof, relay lens means for relaying and projecting the intermediate image onto said observation optical means of the slit lamp, and light intercepting means provided at said intermediate image-forming point and including a plate having a substantially straight line main aperture means disposed on the optical axis of said objective lens system, and alignment aperture means comprising substantially straight line apertures extending transverse to said main aperture means offset from the optical axis of said objective lens system; the main aperture being positioned to intercept the light reflected from the cornea and to pass light reflected from the endothelial cells, and the alignment aperture means being positioned to partially transmit light reflected from the cornea;

whereby when the slit lamp is aligned to coincide the slit of light of the slit illuminating means with an endothelial cell layer of the eye to be examined, the endothelial cell layer is imaged in said main aperture means of said light intercepting means and light reflected by a corneal surface of the eye to be examined is transmitted through said alignment aperture means and substantially intercepted by the plate of said light intercepting means.

5. An attachment as set forth in claim 4 wherein said alignment aperture means includes at least two slit-like openings formed perpendicular to said main aperture means with a spacing between said slit-like openings being of a predetermined value so that they can be used as a scale.

* * * * *